(12) United States Patent
Feng

(10) Patent No.: US 10,674,753 B2
(45) Date of Patent: Jun. 9, 2020

(54) FOOD STORAGE CABINET

(71) Applicant: Shen-Te Feng, Taichung (TW)

(72) Inventor: Shen-Te Feng, Taichung (TW)

( * ) Notice: Subject to any disclaimer, the term of this patent is extended or adjusted under 35 U.S.C. 154(b) by 400 days.

(21) Appl. No.: 15/801,671

(22) Filed: Nov. 2, 2017

(65) Prior Publication Data

US 2019/0124957 A1 May 2, 2019

(51) Int. Cl.
*A23L 3/3418* (2006.01)
*A61L 2/08* (2006.01)
*A23L 3/00* (2006.01)
*A23L 3/28* (2006.01)

(52) U.S. Cl.
CPC .............. *A23L 3/3418* (2013.01); *A23L 3/001* (2013.01); *A23L 3/28* (2013.01); *A61L 2/08* (2013.01); *A23V 2002/00* (2013.01)

(58) Field of Classification Search
CPC .......... A23L 3/001; A23L 3/28; A23L 3/3418; A23V 2002/00; A61L 2/08
USPC .......................................................... 99/451
See application file for complete search history.

(56) References Cited

U.S. PATENT DOCUMENTS 2,425,816 A * 8/1947 Maxson ............... A23L 3/28
62/231
7,836,876 B2 * 11/2010 Schellenberg ........ A47J 39/006
126/268
2005/0077806 A1 * 4/2005 Schellenberg .......... A23L 3/001
312/400
2016/0366919 A1 * 12/2016 van Someren Greve .....................
A23L 3/363

* cited by examiner

*Primary Examiner* — Lorne E Meade
*Assistant Examiner* — Joe E Mills, Jr.
(74) *Attorney, Agent, or Firm* — Che-Yang Chen; Law Office of Michael Chen

(57) ABSTRACT

A food storage cabinet may comprise a main body, an inert gas cylinder, a vacuum unit and a storage container. The main body has a controller which is electrically connected to a motor, and the motor further comprises a spindle connected to a measuring rod to achieve dropping stored food to a scale. The scale is also electrically connected to the controller such that when the preset amount of stored food on the scale is met, the controller is configured to automatically stop the motor. The inert gas cylinder and the vacuum unit are used for maintaining the inner space of the storage container in vacuum and filled with inert gas respectively, thereby keeping the stored food fresh. Also, an operating unit is installed adjacent to the measuring rod of the storage container to drive the measuring rod for dropping stored food manually.

10 Claims, 15 Drawing Sheets

FOOD STORAGE CABINET

FIELD OF THE INVENTION

The present invention relates to a food storage cabinet and more particularly to a food storage cabinet that can prolong the storage time of food and provide a preset amount of storing food for a user at a time.

BACKGROUND OF THE INVENTION

Microorganism and germ are two main substances to spoil food, and people can prolong the storage time of food through destroying or inhibiting their growth. Microorganism and germ are always survived in the right conditions such as adequate water and nutrition and the suitable temperatures. The two most common ways for maintenance of food are freezing and vacuum package, and through these methods, the growth of microorganism can be restrained and foods can be kept for a longer time.

However, the conventional methods for keeping food fresh is insufficient because: (i) even the food is put in freezer or refrigerator, it only can stay fresh for days; and (ii) the vacuum package usually cannot be reuse after torn open. Therefore, there remains a need for a new and improved design for a food storage cabinet to overcome the problems presented above.

SUMMARY OF THE INVENTION

The present invention provides a food storage cabinet which comprises a main body, an inert gas cylinder, a vacuum unit and a storage container. The main body has an interior space, a storage room, and a second room which is configured for withdrawing stored food, and a controller installed in the interior space is electrically connected to a motor. Moreover, the motor comprises a spindle located inside the storage room, and a suction nozzle and an inflated portion are respectively installed on the storage room of the main body. Furthermore, a first dropping opening is formed between the storage room and the second room, and the second room has an air-tight door. The inert gas cylinder controlled by the controller is installed in the interior space of the main body and connected to the inflated portion through a pipe. The vacuum unit controlled by the controller is installed in the interior space of the main body and connected to the suction nozzle through a first vacuum tube. The storage container has a funnel-shaped inner space, and a first connecting member and a second connecting member installed on a side of the storage container are communicated with the inner space. Furthermore, a bottom end of the inner space has a second dropping opening. A measuring rod penetrating through the storage container is located adjacent to the second dropping opening, and the measuring rod further comprises a measuring tank located at a position corresponding to and blocking the second dropping opening. The storage container is put and secured inside the storage room of the main body, and the first connecting member and the second connecting member are respectively connected to the inflated portion and the suction nozzle.

In one embodiment, an operating unit, which is configured to operate the measuring rod to drop stored food manually, is installed adjacent to the measuring rod of the storage container.

In another embodiment, the operating unit further comprises a rod piece, a first spring, a toothed bar and a toothed disc. An end of the rod piece connected to the first spring is adapted to stick out of the storage container for a user to push while another end of the rod piece is engaged with the toothed bar. The toothed disc is installed on the storage container, and a gear rod extending from a surface of the toothed disc is configured to engage with the toothed bar to have synchronous movements. Moreover, a gear is installed on the spindle of the motor to engage with the toothed disc such that by pushing the rod piece, the toothed bar is configured to drive the gear and the measuring rod through the gear rod and the toothed disc to have spin movements synchronously.

In still another embodiment, the storage container has a locating groove, and a column extended from a surface of the toothed bar is adapted to be inserted and move along the locating groove, thereby achieving the engaging and disengaging processes between the toothed bar and the gear rod.

In a further embodiment, a lateral surface of the storage container has a cap located at a position corresponding to an end of the measuring rod, so that after the cap is removed, the measuring rod can be directly pulled out and a user can control the amount of single dropping by changing a measuring rod having a desired-sized measuring tank.

In still a further embodiment, a top end of the inner space is connected to an openable lid; the storage container has a handle which is communicated with the inner space, and the handle further comprises a release button which is adapted to release vacuum status of the inner space to enable the lid to be opened.

In yet a further embodiment, a second vacuum tube is connected between the vacuum unit and a vacuum nozzle, and the vacuum nozzle is communicated with the second room to create a vacuum in the second room.

In a particular embodiment, the second room comprises a germicidal lamp and a scale, which are electrically and respectively connected to the controller.

In a preferred embodiment, the first connecting member has a second spring and a first ball body installed therein, and the second spring is configured to bear against the first ball body and an end of the first connecting member at two ends thereof to push the first ball body outwardly; and the second connecting member comprises a third spring and a second ball body installed therein, and the third spring is configured to bear against the second ball body and an end of the second connecting member at two ends thereof to push the second ball body outwardly. Therefore, the storage container is configured to be maintained in vacuum or be filled with inert gas both when been secured in and taken out from the main body. The suction nozzle has a protruding push rod which is configured to push away the first ball body of the first connecting member.

In an advantageous embodiment, the storage container comprises a metal piece, and the storage room has a magnetic member which is configured to attract and hold the metal piece, thereby securing a position of the storage container.

Comparing with conventional food storage cabinet, the present invention is advantageous because: (i) the vacuum unit is configured to create vacuum in the inner space of the storage container and the second room, thereby form a negative pressure to keep stored food fresh; (ii) the inert gas cylinder can pump inert gas into the inner space of the storage container to prolong the storage time for most of food and improve food safety; (iii) the second room of the main body is also maintained in vacuum state such that when the stored food is dropped from the measuring rod to the second room, the inner space can be maintained in vacuum state, and after dropping the stored food, the storage container only need to add a small amount of inert gas from the inert gas cylinder, thereby lowering the cost; (iv) after the measuring rod is spun, the stored food in the measuring tank is dropped on a container of the scale, and the controller is adapted to automatically stop the motor when the preset amount calculated by the scale is met; (v) the invention has the operating unit to spin the measuring rod and then drop the stored food in the measuring tank to a container of the scale, thereby achieving dropping process manually; (vi) through the engagement between the toothed bar and the gear rod and between the toothed disc and the gear, the measuring rod can be driven and axially spun a full circle when the rod piece is pushed one time such that a user can easily control the dropping amount to the container of the scale; (vii) a user can remove the cap from the storage container, and directly pull out and change a measuring rod which has a desired-sized measuring tank to control the amount of single dropping; (viii) the second spring of the first connecting member and the third spring of the second connecting member are respectively configured to push the first ball body and the second ball body outwardly, thereby maintaining the sealed state of storage container even when the storage container is pull out of the main body; and (ix) the storage container is kept in vacuum state or filled with inert gas such that different kinds of foods can be stored in different storage containers which are configured to selectively and quickly put into the main body.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

Figure 18:
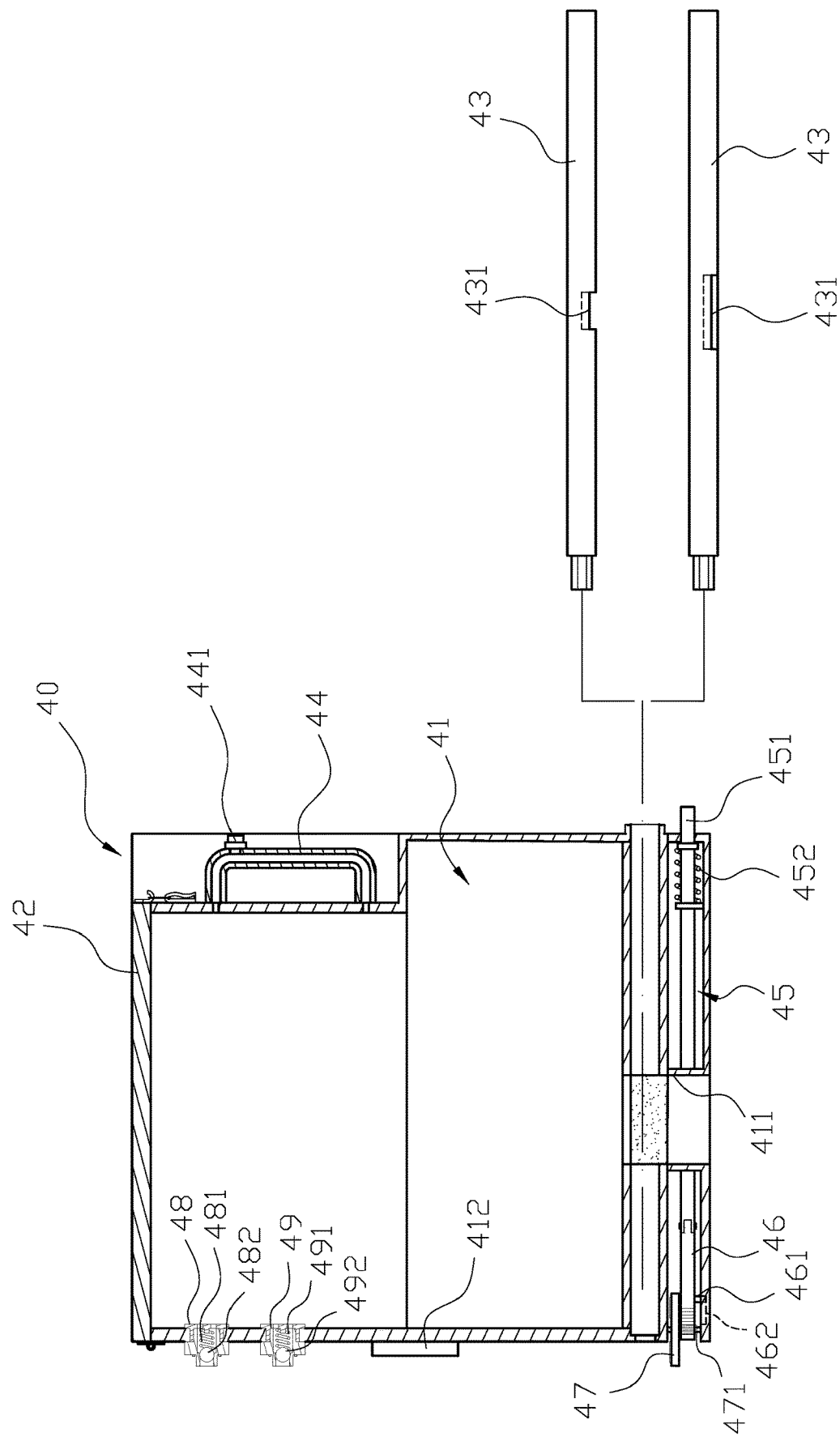
FIG. 18 is a schematic view illustrating the measuring rod is changed.

In order to further understand the goal, characteristics and effect of the present invention, a number of embodiments along with the drawings are illustrated as following:

Referring to FIGS. 1, 2, 5 and 8, the present invention provides a food storage cabinet which comprises a main body (10), an inert gas cylinder (20), a vacuum unit (30) and a storage container (40). The main body (10) has an interior space (11), a storage room (12), and a second room (13) which is configured for withdrawing stored food, and a controller (14) installed in the interior space (11) is electrically connected to a motor (15). Moreover, the motor (15) comprises a spindle (151) located inside the storage room (12), and a suction nozzle (16) and an inflated portion (161) are respectively installed on the storage room (12) of the main body (10). Furthermore, a first dropping opening (121) is formed between the storage room (12) and the second room (13), and the second room (13) has an air-tight door (131). In addition, the second room (13) comprises a germicidal lamp (17) and a scale (18), which are electrically and respectively connected to the controller (14) to achieve sterilization and weighing processes before the stored food is taken out by a user. The inert gas cylinder (20) controlled by the controller (14) is installed in the interior space (11) of the main body (10) and connected to the inflated portion (161) through a pipe (21), and the inert gas cylinder (20) is filled with nitrogen. The vacuum unit (30) controlled by the controller (14) is installed in the interior space (11) of the main body (10) and connected to the suction nozzle (16) through a first vacuum tube (31). Additionally, a second vacuum tube (32) is connected between the vacuum unit (30) and a vacuum nozzle (33), and the vacuum nozzle (33) is communicated with the second room (13) to create a vacuum in the second room (13). The storage container (40) has a funnel-shaped inner space (41), and a first connecting member (48) and a second connecting member (49) installed on a side of the storage container (40) are communicated with the inner space (41). Furthermore, a bottom end of the inner space (41) has a second dropping opening (411) while a top end thereof is connected to an openable lid (42). A measuring rod (43) penetrating through the storage container (40) is located adjacent to the second dropping opening (411), and the measuring rod (43) further comprises a measuring tank (431) located at a position corresponding to and blocking the second dropping opening (411). Moreover, a lateral surface of the storage container (40) has a cap (432) located at a position corresponding to an end of the measuring rod (43), so that after the cap (432) is removed, the measuring rod (43) can be directly pulled out and a user can control the amount of single dropping by changing a measuring rod (43) having a desired-sized measuring tank (431) (as shown in FIG. 18).

The storage container (40) is put and secured inside the storage room (12) of the main body (10), and the storage room (12) further has a magnetic member (122). Moreover, the storage container (40) comprises a metal piece (412), and the magnetic member (122) is configured to attract and hold the metal piece (412), thereby securing a position of the storage container (40). The first connecting member (48) and the second connecting member (49) are respectively connected to the inflated portion (161) and the suction nozzle (16). Also, the first connecting member (48) has a second spring (481) and a first ball body (482) installed therein, and the second spring (481) is configured to bear against the first ball body (482) and an end of the first connecting member (48) at two ends thereof to push the first ball body (482) outwardly. Similarly, the second connecting member (49) comprises a third spring (491) and a second ball body (492) installed therein, and the third spring (491) is configured to bear against the second ball body (492) and an end of the second connecting member (49) at two ends thereof to push the second ball body (492) outwardly. Therefore, the storage container (40) is configured to be maintained in vacuum or be filled with inert gas both when been secured in and taken out from the main body (10). In addition, the suction nozzle (16) has a protruding push rod (162) which is configured to push away the first ball body (482) of the first connecting member (48). The measuring rod (43) is axially connected to the spindle (151) of the motor (15) to have spin movement synchronously. The inert gas cylinder (20) and the vacuum unit (30) are used for maintaining the inner space (41) of the storage container (40) in vacuum and filled with inert gas respectively. The storage container (40) has a handle (44) which is communicated with the inner space (41), and the handle (44) further comprises a release button (441) which is adapted to release vacuum status of the inner space (41) to enable the lid (42) to be opened. The motor (15) is configured to axially spin the measuring rod (43), and the stored food, especially granular food, in the measuring tank (431) is adapted to be dropped and pass through the first dropping opening (121) into the second room (13), thereby providing a fixed amount of stored food at a time for a user.

In actual application, referring to FIGS. 1 to 9, through the controller (14), the main body (10) is electrically connected to the inert gas cylinder (20), the vacuum unit (30), the motor (15), germicidal lamp (17) and the scale (18). A user can input desired parameters to the controller (14) to accomplish following functions: (i) the controller (14) can control the vacuum unit (30) to create vacuum in the storage container (40) through the first vacuum tube (31) and the suction nozzle (16); (ii) the controller (14) can draw air through the second vacuum tube (32) and the vacuum nozzle (33) to create vacuum in the second room (13); (iii) the controller (14) can control the inert gas cylinder (20) to pump inert gas into the storage container (40) through the pipe (21) and the inflated portion (161); (iv) the controller (14) can control the motor (14) to axially spin the measuring rod (43) of the storage container (40), thereby getting the fixed amount of stored food through the measuring tank (431); (v) the germicidal lamp (17) can disinfect the stored food in the second room (13) through UV-light; and (vi) the scale (18) is configured to measure total weight of dropped food, and the controller (14) is adapted to stop the motor (15) when the desired amount of stored food is met.

More specifically, in a preferred embodiment, the food can be put into the inner space (41) of the storage container (40) when the lid (42) is opened, and the storage container (40) is slidely put into the storage room (12) of the main body (10) such that the measuring rod (43) can be directly inserted and connected to the spindle (151). In one embodiment, the measuring rod (43) and the spindle (151) are connected in a manner of a column with polygonal cross section and a corresponding polygonal hole. After the storage container (40) is put into the main body (10), the suction nozzle (16) and the inflated portion (161) are respectively and air-tightly connected to the first connecting member (48) and the second connecting member (49). Moreover, the second spring (481) and the third spring (491) are respectively abutted against the first ball body (482) and the second ball body (492) to enable the first connecting member (48) and the second connecting member (49) to be one-way valves. When the first connecting member (48) and the second connecting member (49) are respectively connected to the suction nozzle (16) and the inflated portion (161), the push rod (162) is configured to push the first ball body (482), and the inner space (41) is communicated with the first vacuum tube (31). Meanwhile, when the storage container (40) is put all the way in the storage room (12), the metal piece (412) of the storage container (40) is configured to be attracted and held by the magnetic member (122) of the storage room (12), thereby securing the position of the storage container (40), the connection between the suction nozzle (16) and the first connecting member (48), and the connection between the inflated portion (161) and the second connecting member (49). On the other hand, the storage container (40) can be moved and pulled out of the main body (10) when force is applied overcoming the magnetic force between the metal piece (412) and the magnetic member (122).

Figure 19:
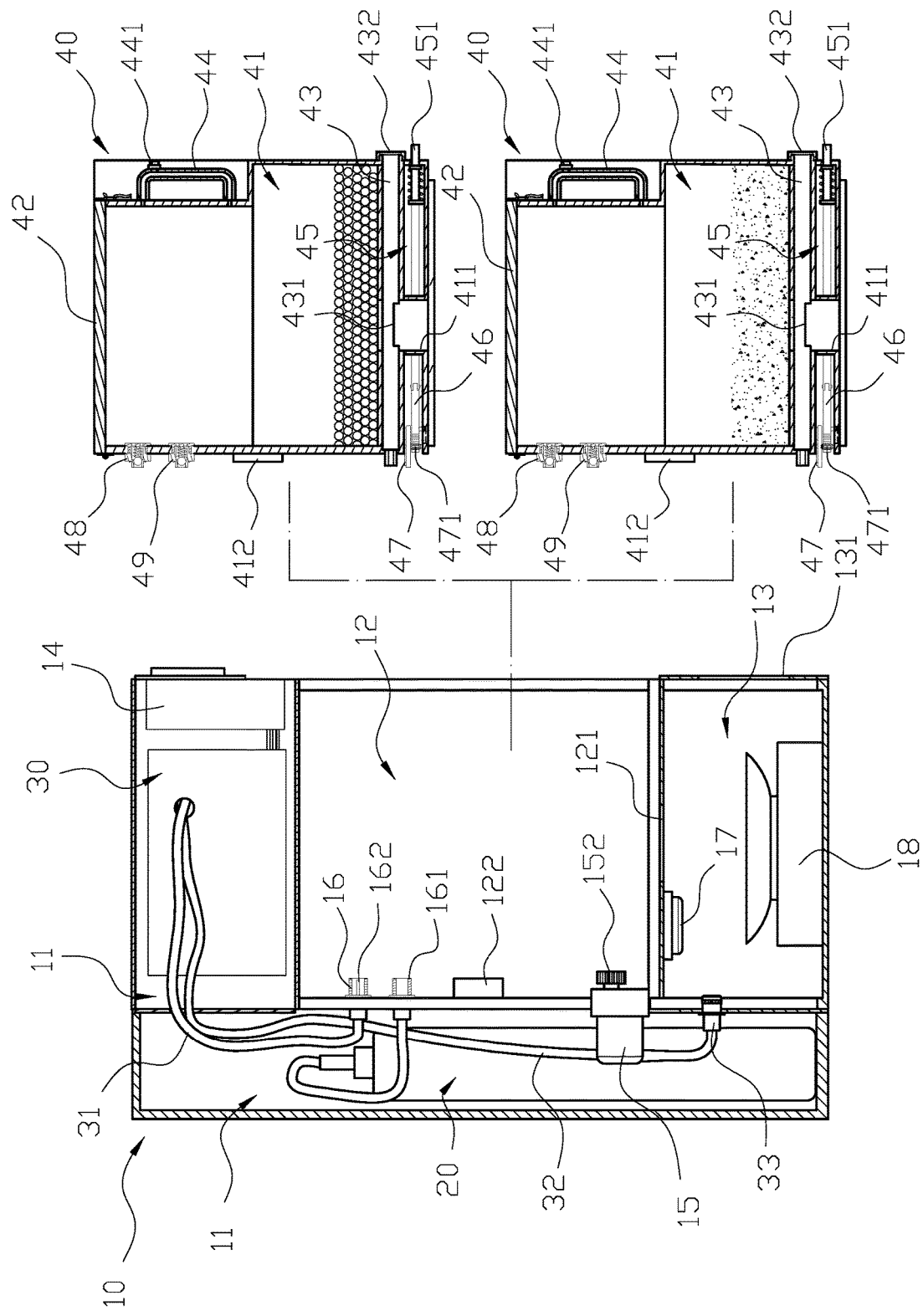
FIG. 19 is a schematic view illustrating the storage container is changed.

Referring to FIG. 19, the second spring (481) of the first connecting member (48) and the third spring (491) of the second connecting member (49) are respectively configured to push the first ball body (482) and the second ball body (492) outwardly, thereby maintaining the sealed state of storage container (40) even when the storage container (40) is pull out of the main body (10). Namely, the storage container (40) is kept in vacuum state or filled with inert gas such that different kinds of foods can be stored in different storage containers (40) which are configured to selectively and quickly put into the main body (10). When the storage container (40) is put in the storage room (12) of the main body (10), the measuring rod (43) is connected to the motor (15) while the second connecting member (49) and the first connecting member (48) are respectively connected to the inert gas cylinder (20) and the vacuum unit (30). The vacuum unit (30) is configured to create vacuum in the inner space (41) of the storage container (40) and the second room (13), thereby form a negative pressure to keep stored food fresh. Moreover, the inert gas cylinder (20) can pump inert gas into the inner space (41) of the storage container (40) to prolong the storage time for most of food and improve food safety. Furthermore, the second room (13) of the main body (10) is also maintained in vacuum state such that when the stored food is dropped from the measuring rod (43) to the second room (13), the inner space (41) can be maintained in vacuum state. Therefore, after dropping the stored food, the storage container (40) only need to add a small amount of inert gas from the inert gas cylinder (20), thereby lowering the cost.

Figure 1:
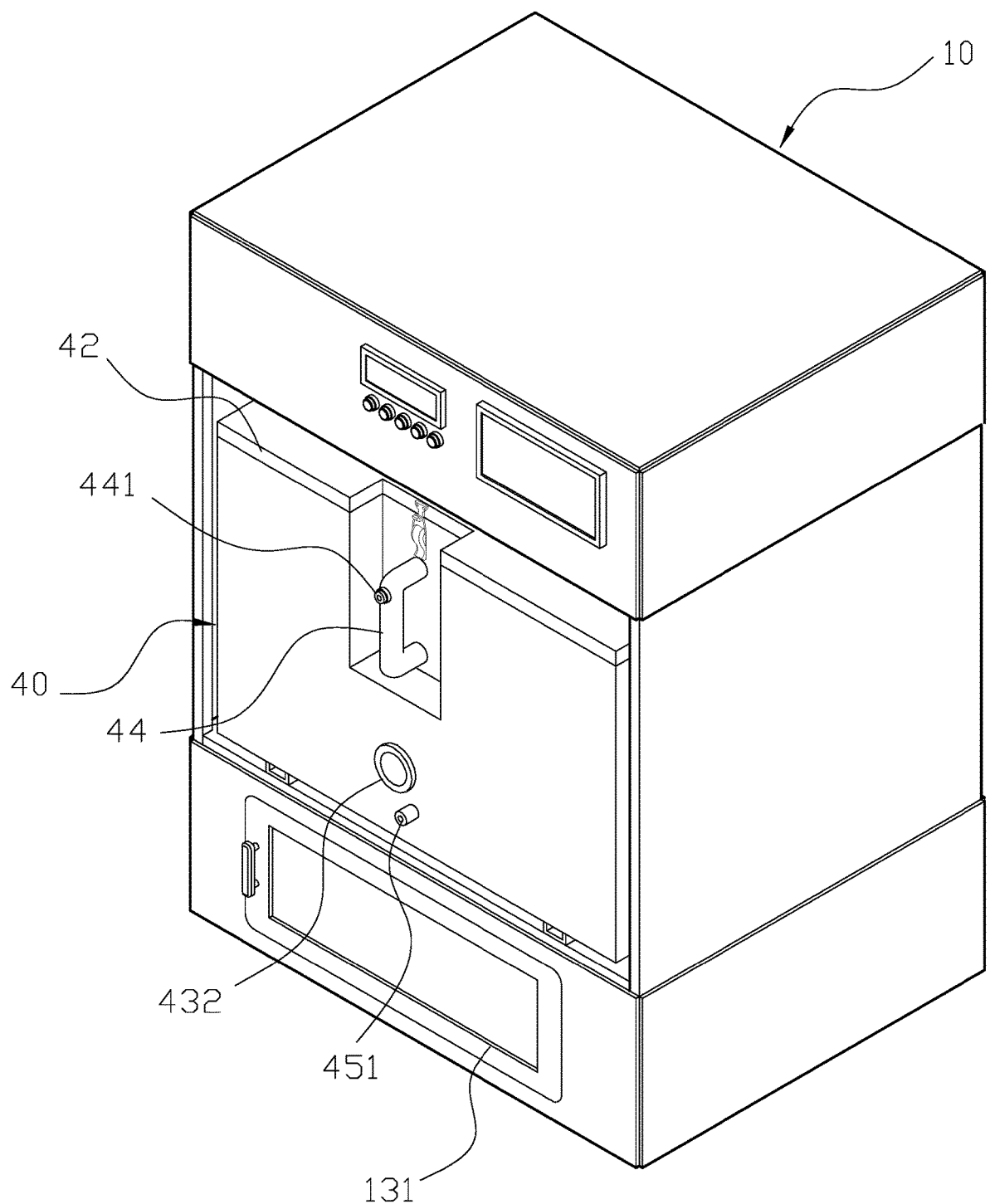
FIG. 1 is a three-dimensional assembly view of a food storage cabinet in the present invention.
Figure 2:
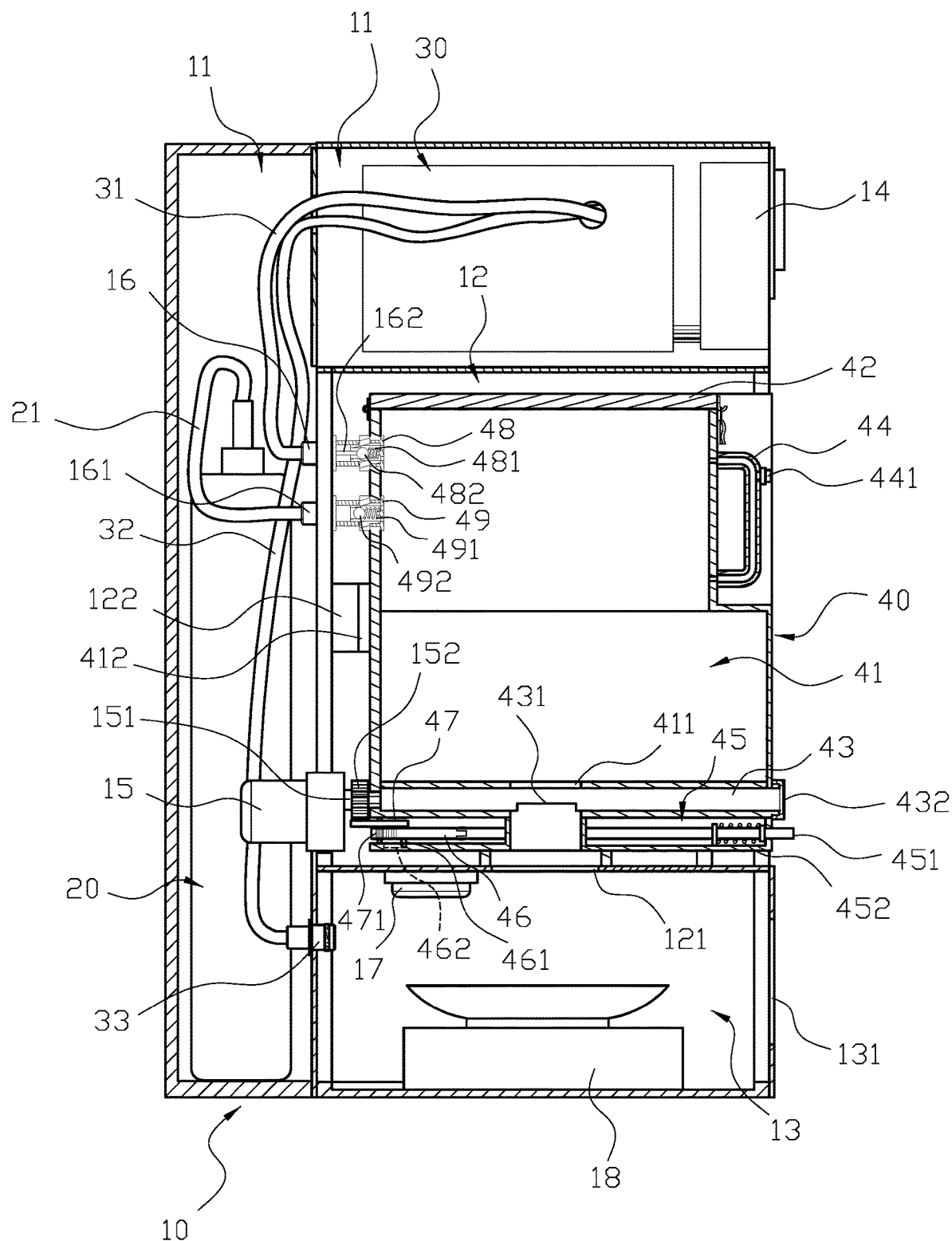
FIG. 2 is a sectional view of the food storage cabinet in the present invention.
Figure 3:
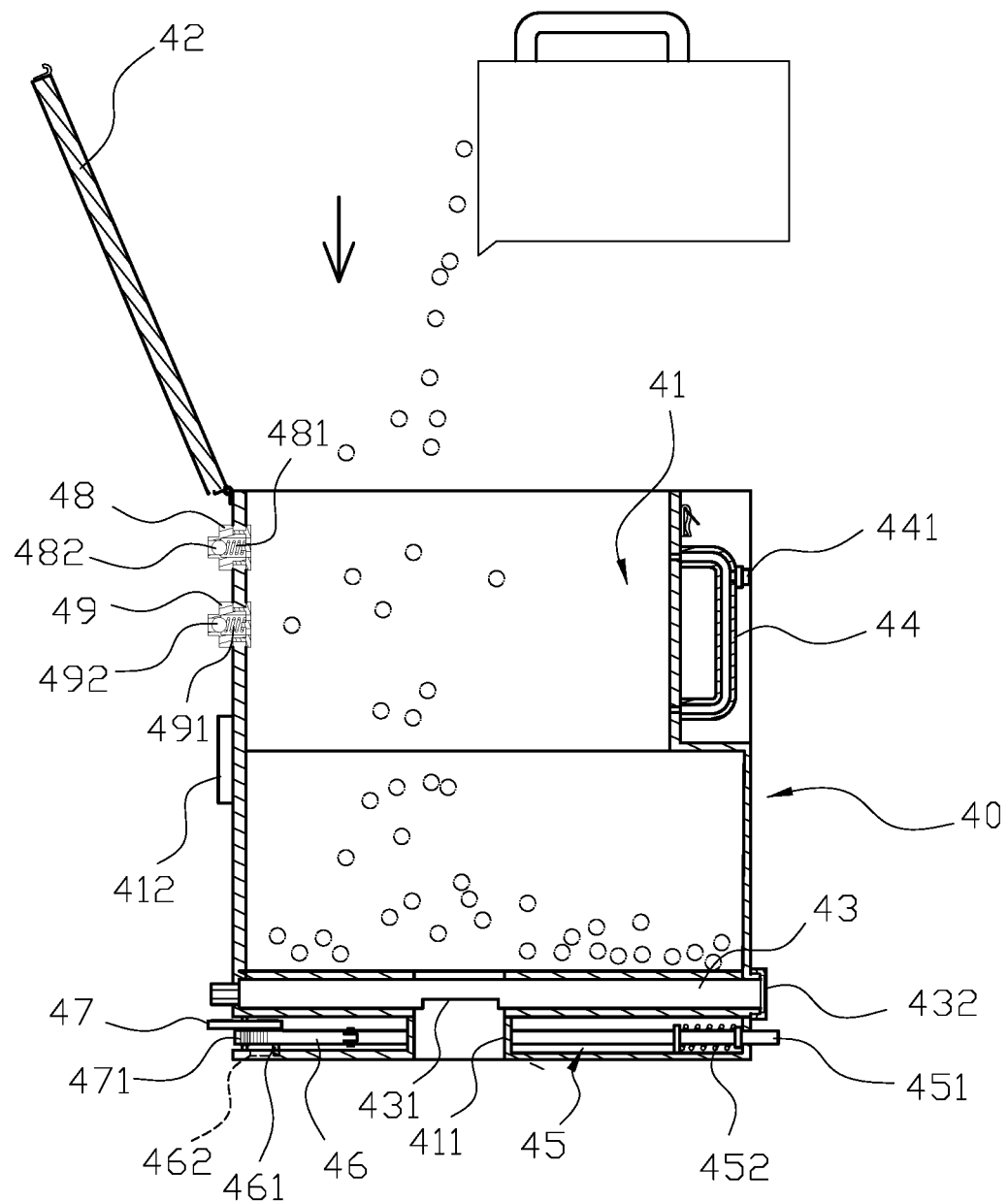
FIG. 3 is a schematic view illustrating food is filled in a storage container of the food storage cabinet in the present invention.
Figure 4:
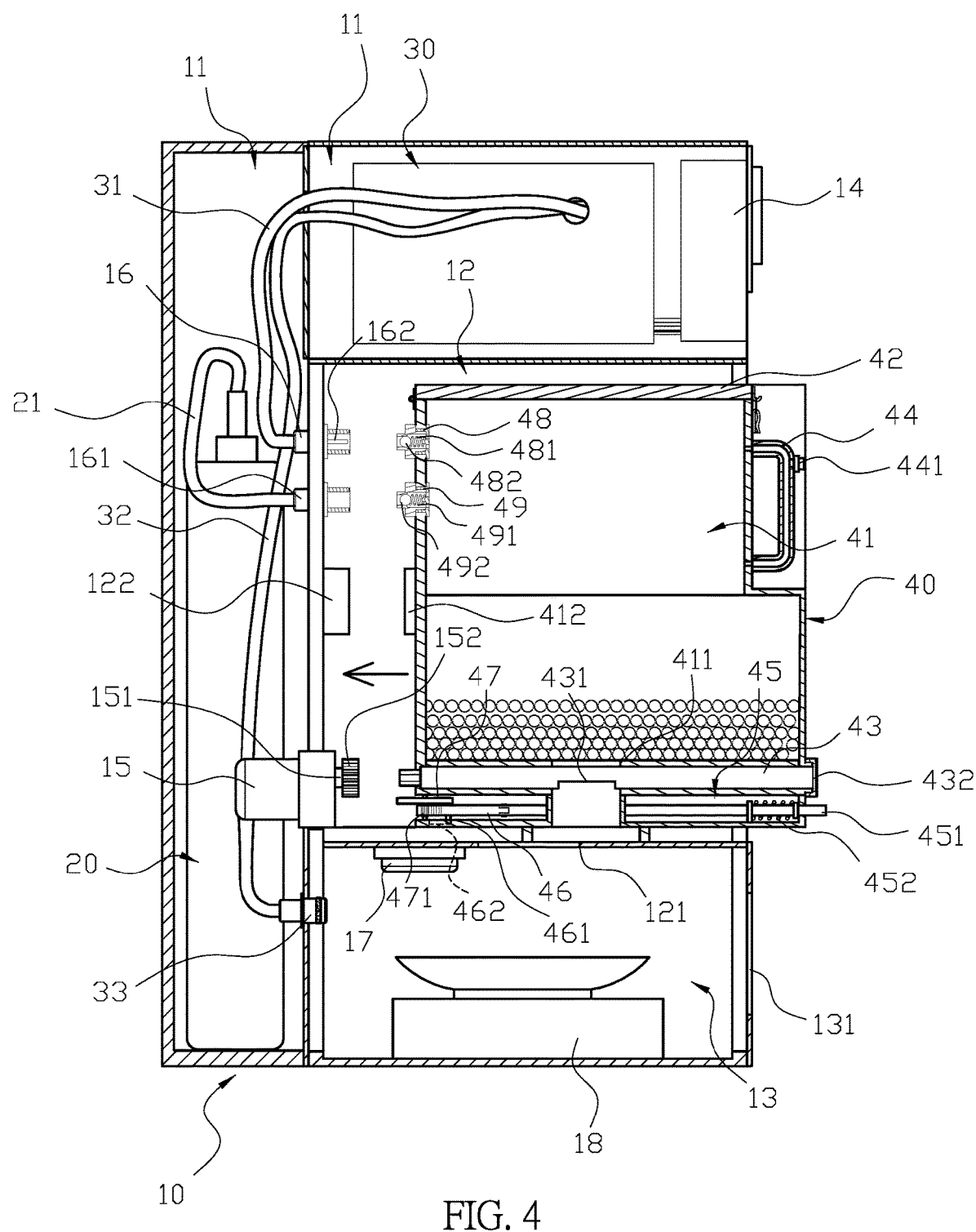
FIG. 4 is a diagram illustrating the storage container is put into a main body of the food storage cabinet in the present invention.
Figure 5:
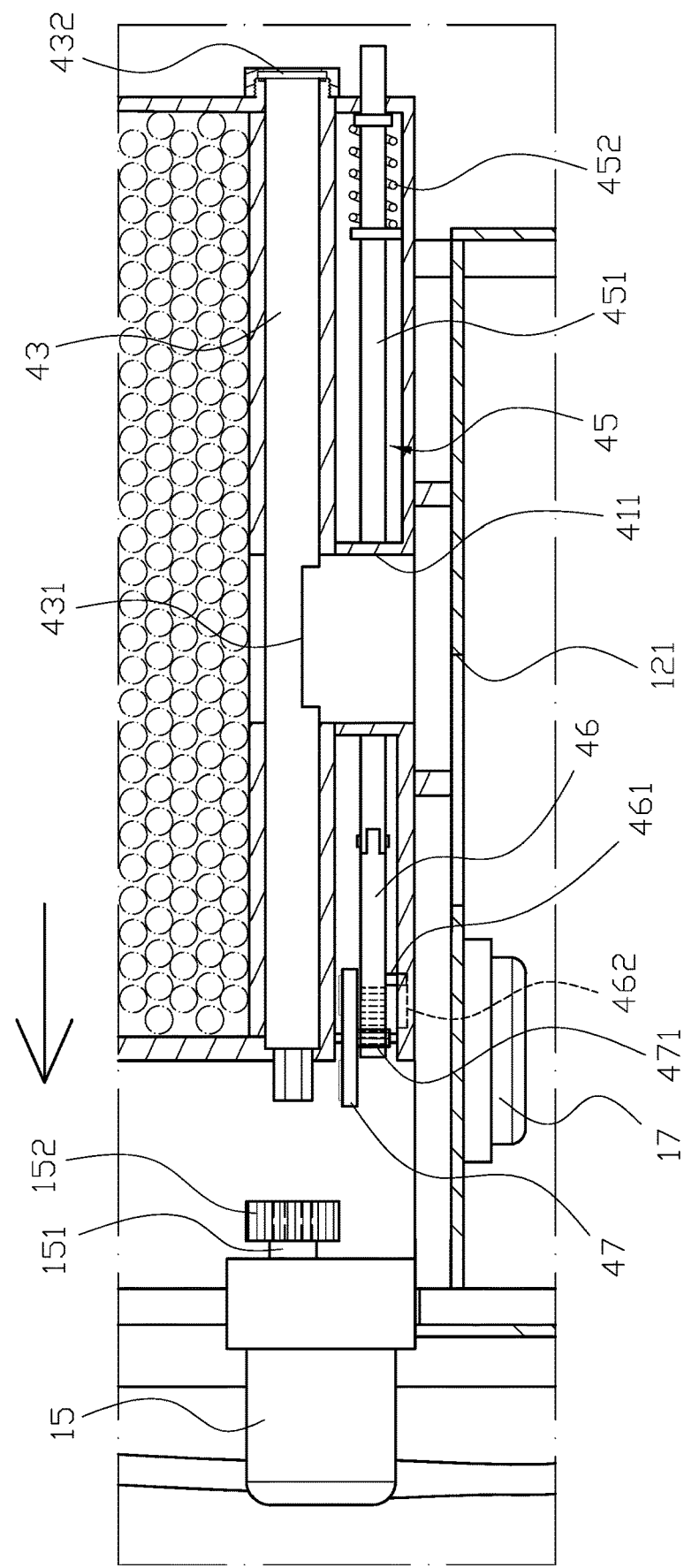
FIG. 5 is a partial enlarged view of FIG. 4.
Figure 6:
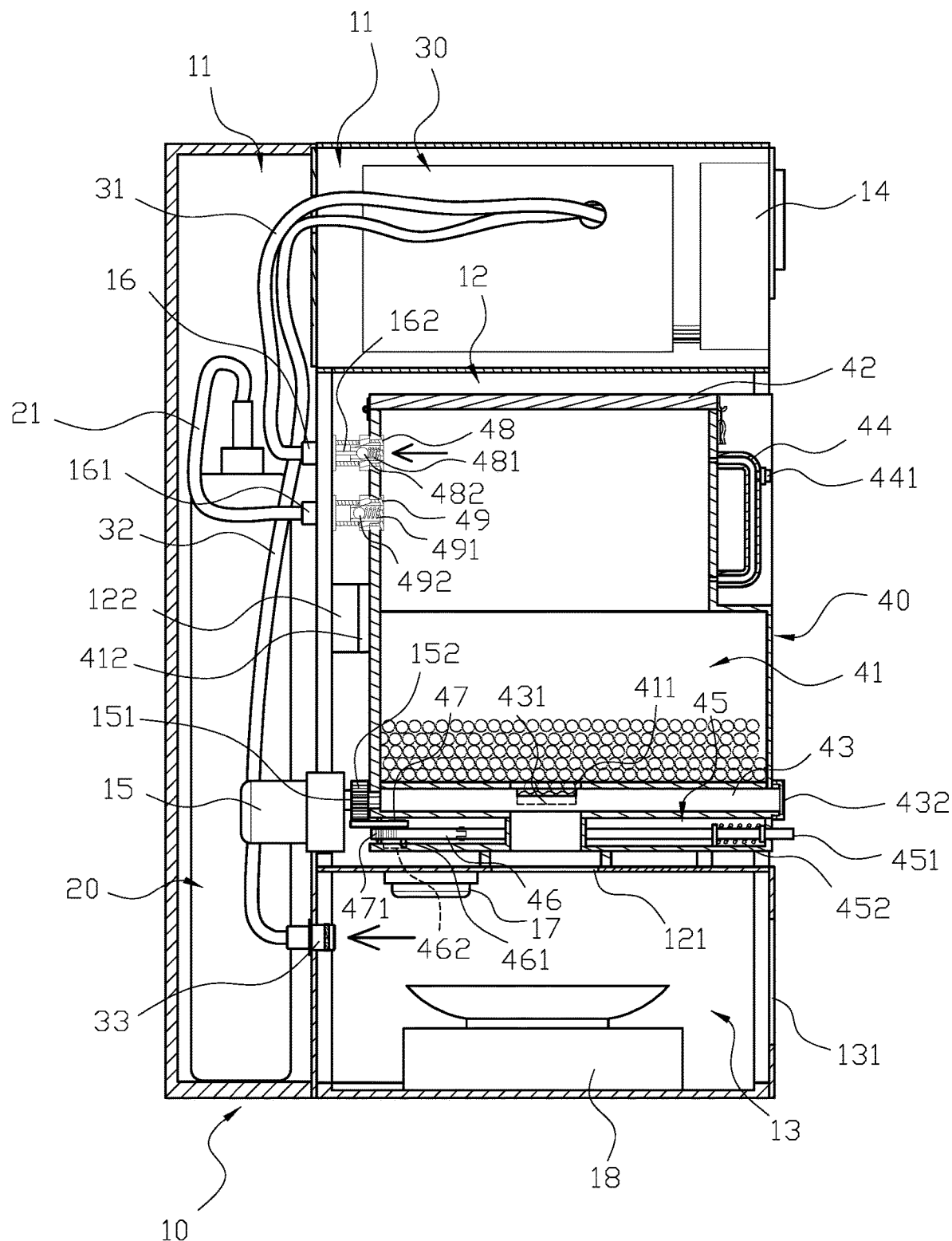
FIG. 6 is a schematic view illustrating the food storage cabinet of the present invention is under vacuum process.
Figure 7:
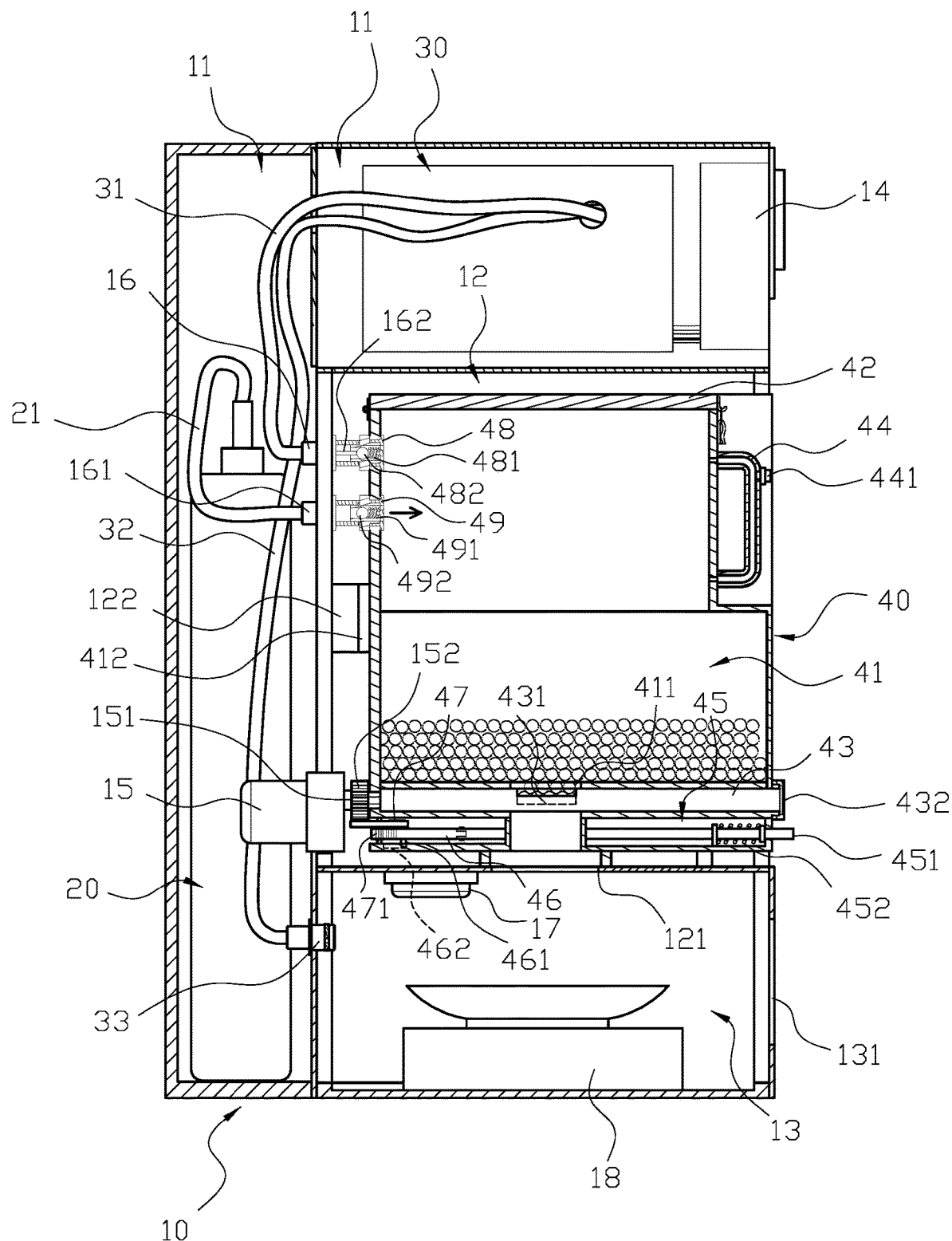
FIG. 7 is a schematic view illustrating an inert gas is pumped into the food storage cabinet of the present invention.
Figure 8:
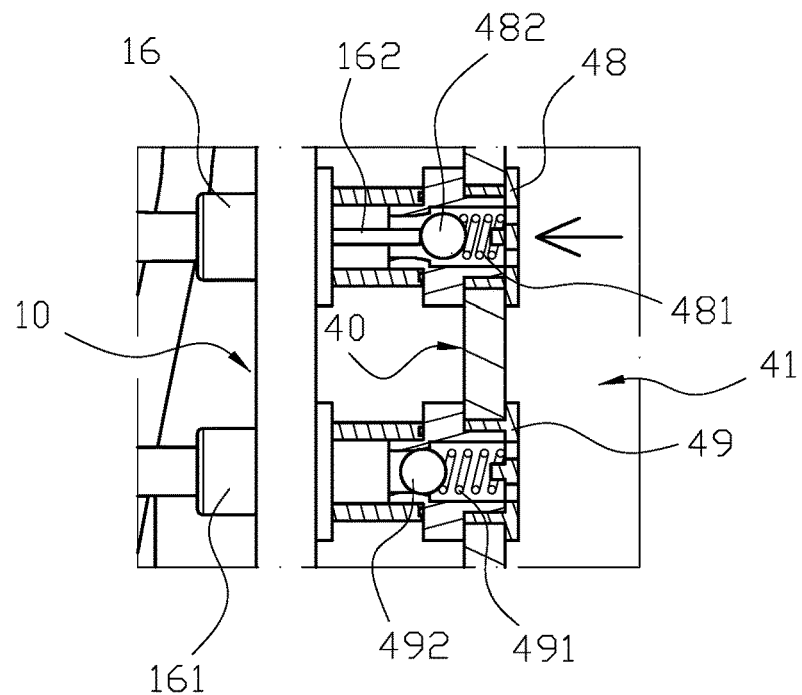
FIG. 8 is a partial enlarged view of FIG. 6.
Figure 9:
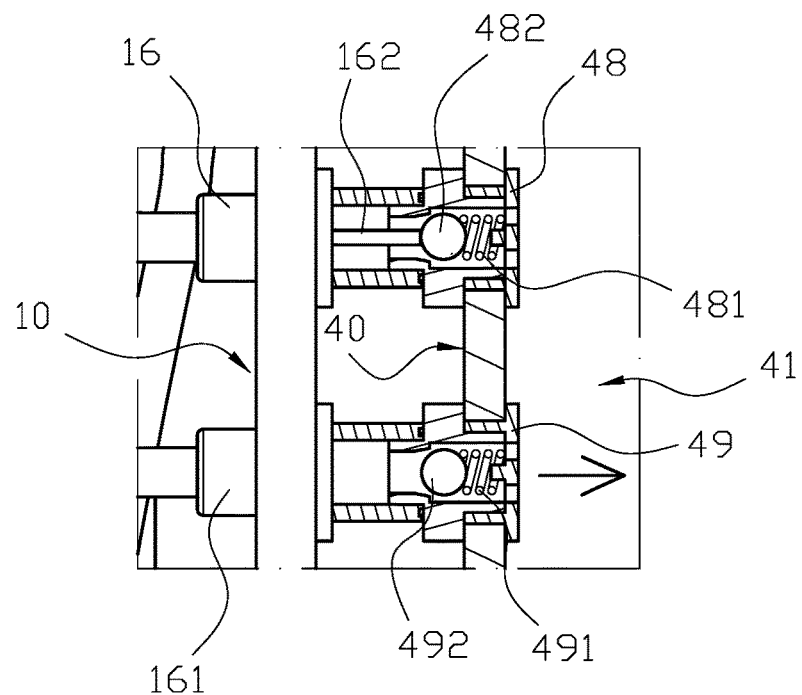
FIG. 9 is a partial enlarged view of FIG. 7.
Figure 10:
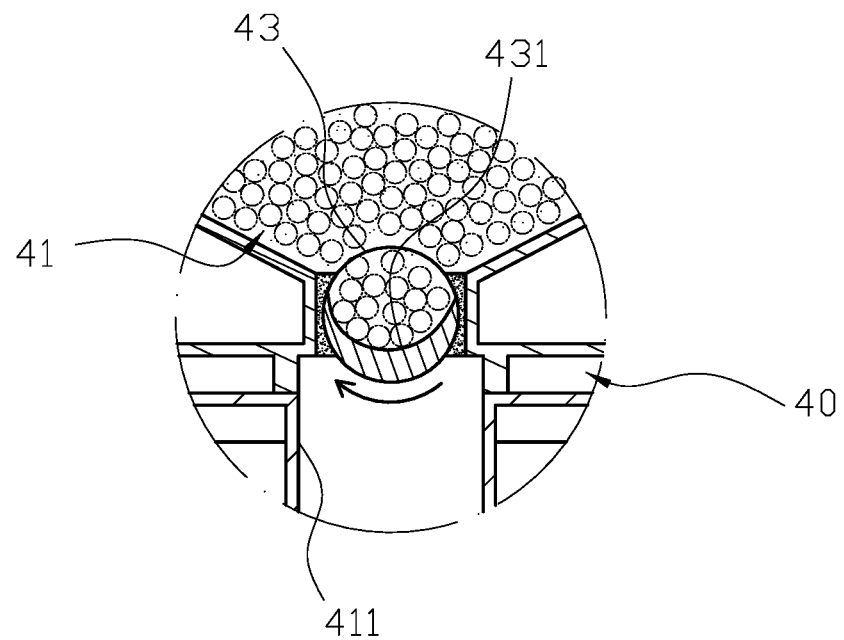
FIG. 10 is the first schematic view illustrating a fixed amount of stored food is automatically dropped from a measuring tank of a measuring rod to a scale of the food storage cabinet in the present invention.
Figure 11:
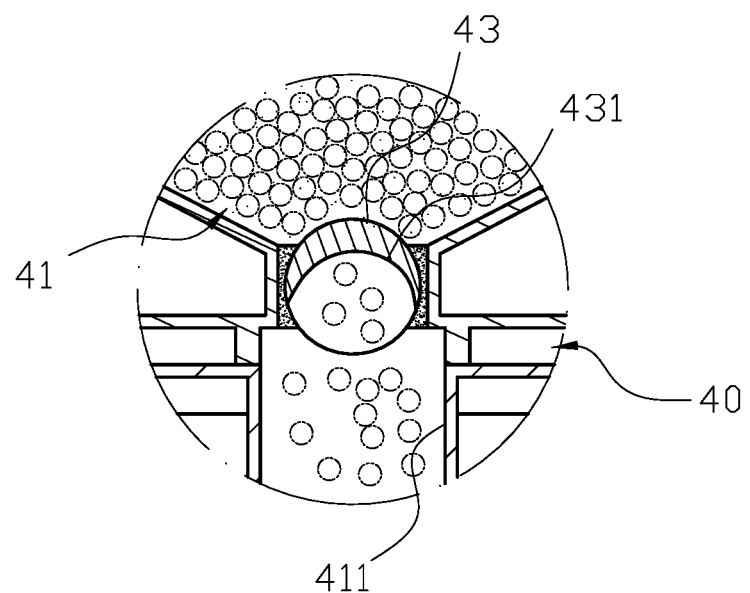
FIG. 11 is the second schematic view illustrating the fixed amount of stored food is automatically dropped from the measuring tank to the scale of the food storage cabinet in the present invention.
Figure 12:
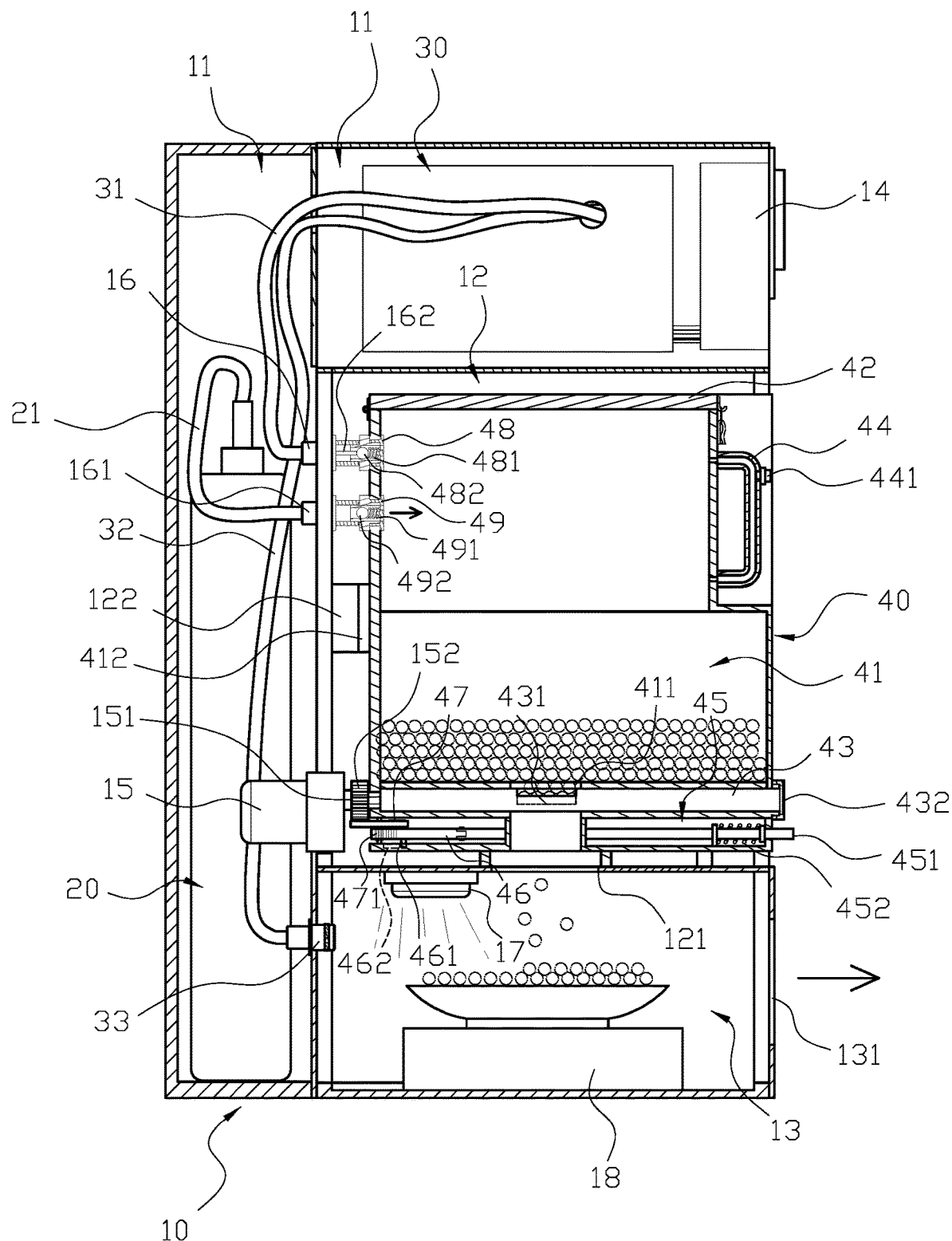
FIG. 12 is the third schematic view illustrating the fixed amount of stored food is automatically dropped from the measuring tank to the scale of the food storage cabinet in the present invention.
Figure 13:
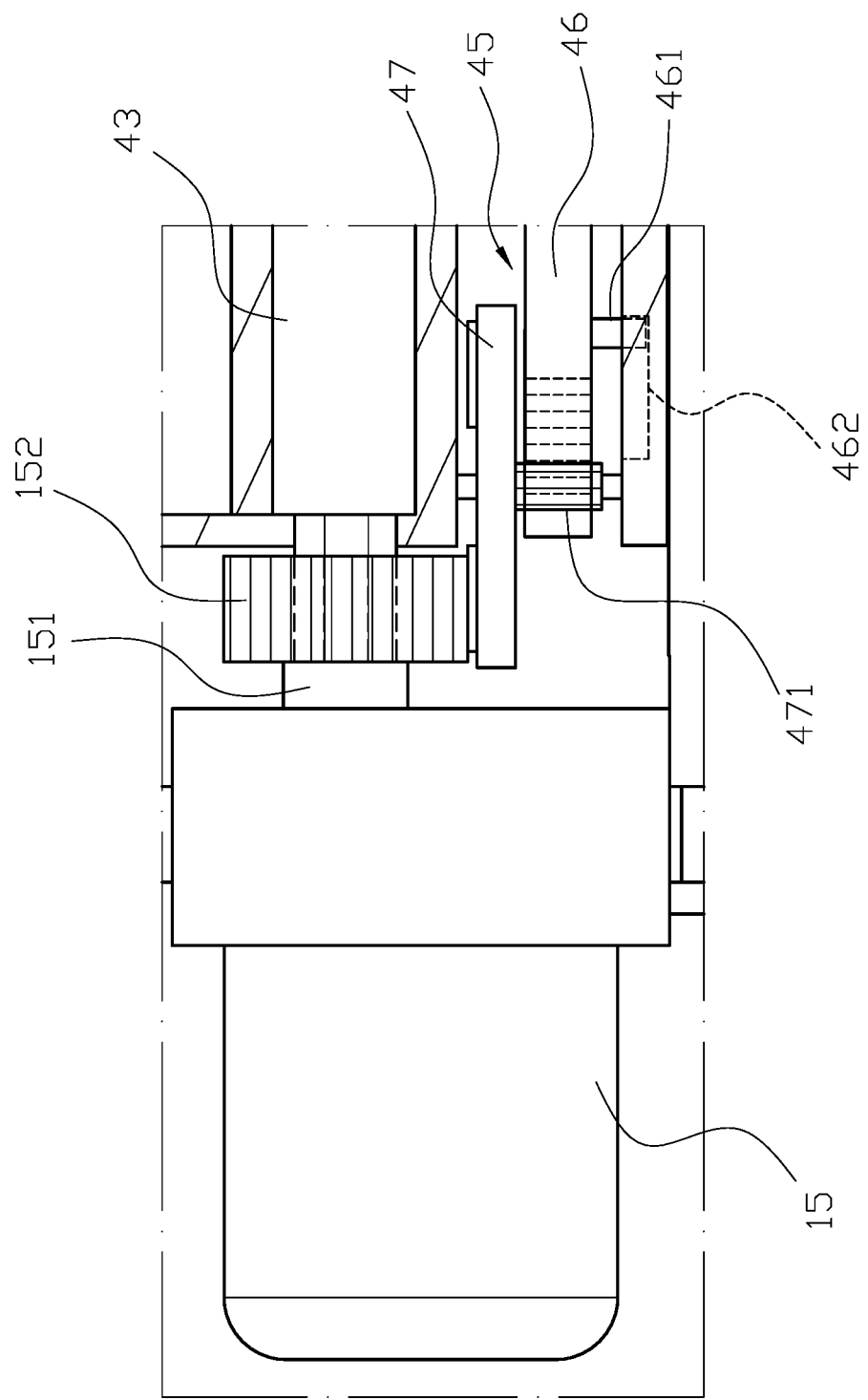
FIG. 13 is a partial enlarged view of an operating unit of the food storage cabinet in the present invention.
Figure 14:
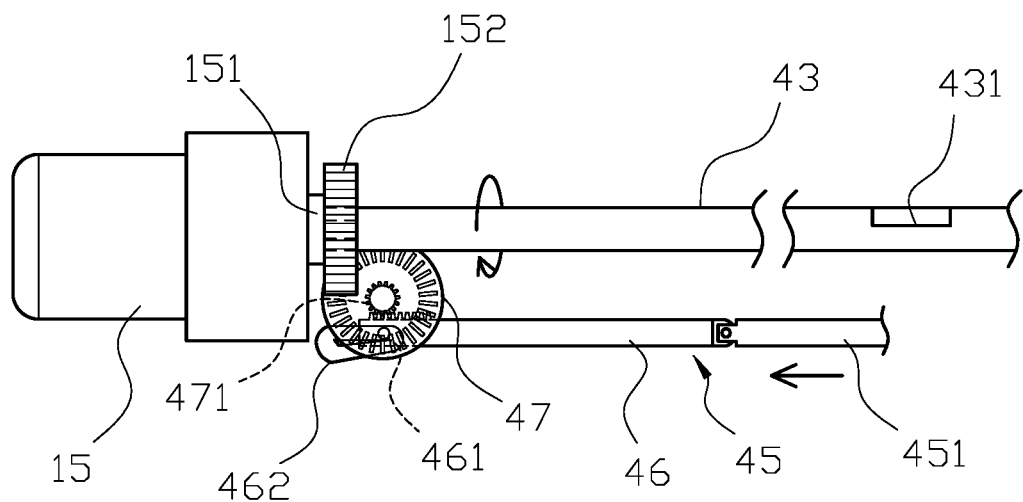
FIG. 14 is a schematic view illustrating the operating unit operates the measuring rod to enable the measuring tank to drop the fixed amount of stored food therefrom manually.
Figure 15:
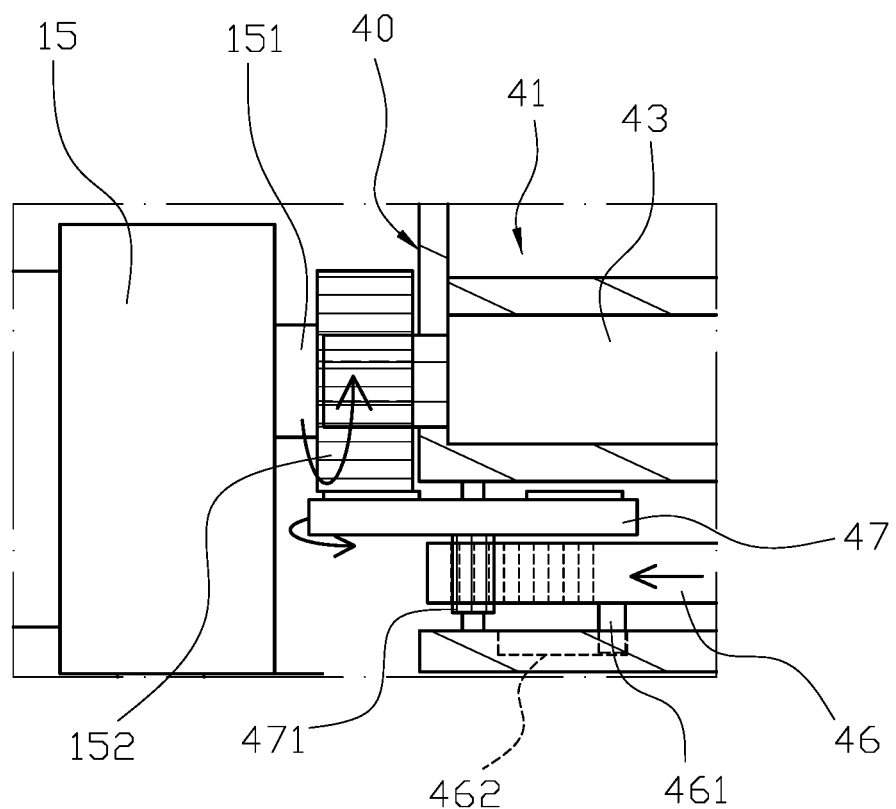
FIG. 15 is the second schematic view illustrating the operating unit operates the measuring rod to enable the measuring tank to drop the fixed amount of stored food therefrom manually.
Figure 16:
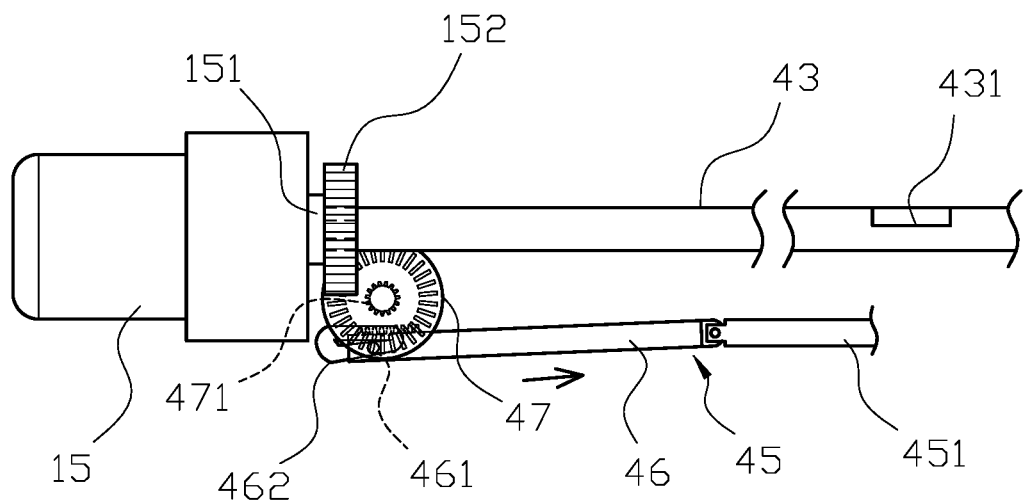
FIG. 16 is the third schematic view illustrating the operating unit operates the measuring rod to enable the measuring tank to drop the fixed amount of stored food therefrom manually.
Figure 17:
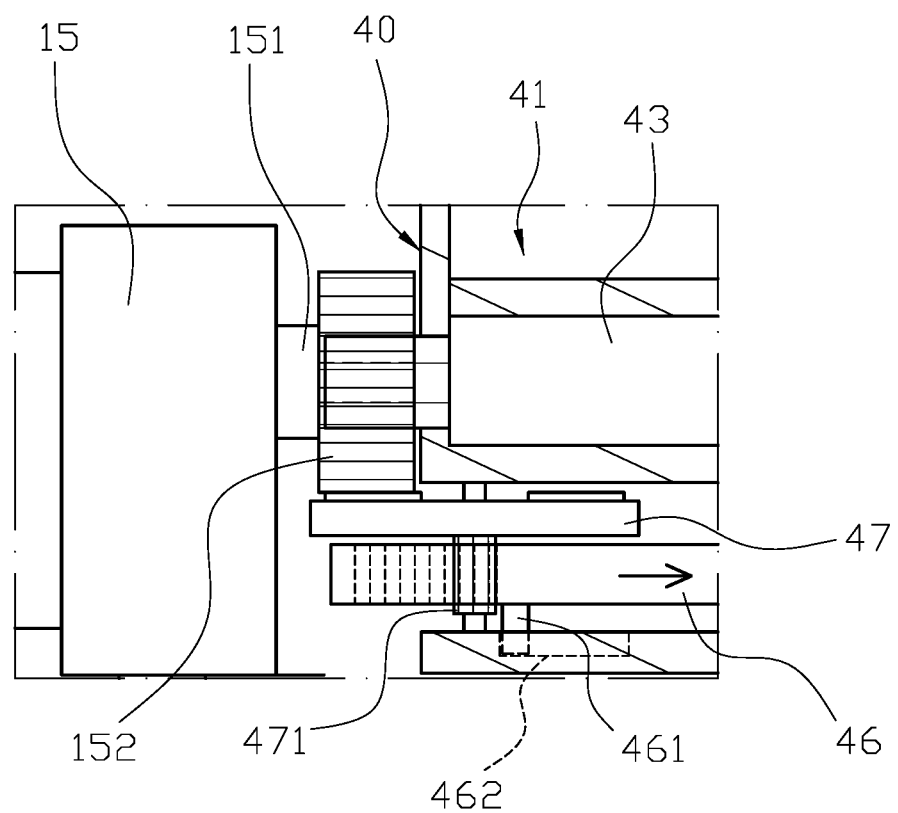
FIG. 17 is the fourth schematic view illustrating the operating unit operates the measuring rod to enable the measuring tank to drop the fixed amount of stored food therefrom manually.

Referring to FIGS. 10 and 11, through the controller (14), a user can preset the amount of stored food needed to be taken out for a batch. Moreover, the controller (14) is configured to axially spin the measuring rod (43) through the spindle (151) of the motor (15). The measuring rod (43) is configured to be positioned between the second dropping opening (411) and the first dropping opening (121), and since the inner space (41) of the storage container (40) is funnel-shaped, the stacked stored food in the inner space (41) is configured to tend to move toward and into the measuring tank (431) of the measuring rod (43). After the measuring rod (43) is spun, the stored food in the measuring tank (431) is dropped on a container of the scale (18), and the controller (14) is adapted to stop the motor (15) when the preset amount calculated by the scale (18) is met. Thereafter, the germicidal lamp (17) is configured to disinfect the stored food in the second room (13) through UV-light, and then a user can open the air-tight door (131) to take out the stored food. Moreover, after the stored food is taken and the air-tight door (131) is closed, and the vacuum unit (30) is adapted to re-create a vacuum in the second room (13).

In another embodiment, referring to FIGS. 5 and 12 to 17, an operating unit (45), which is configured to operate the measuring rod (43) to drop stored food, is installed adjacent to the measuring rod (43) of the storage container (40), and the operating unit (45) further comprises a rod piece (451), a first spring (452), a toothed bar (46) and a toothed disc (47). An end of the rod piece (451) connected to the first spring (452) is adapted to stick out of the storage container (40) for a user to push while another end of the rod piece (451) is engaged with the toothed bar (46). The toothed disc (47) is installed on the storage container (40), and a gear rod (471) extending from a surface of the toothed disc (47) is configured to engage with the toothed bar (46) to have synchronous movements. Moreover, a gear (152) is installed on the spindle (151) of the motor (15) to engage with the toothed disc (47) such that by pushing the rod piece (451), the toothed bar (46) is configured to drive the gear (152) and the measuring rod (43) through the gear rod (471) and the toothed disc (47) to have spin movements synchronously, thereby dropping stored food in the measuring tank (431) manually. In addition, the storage container (40) has a locating groove (462), and a column (461) extended from a surface of the toothed bar (46) is adapted to be inserted and move along the locating groove (462), thereby achieving the engaging and disengaging processes between the toothed bar (46) and the gear rod (471). Also, through the engagement between the toothed bar (46) and the gear rod (471) and between the toothed disc (47) and the gear (52), the measuring rod (43) can be driven and axially spun a full circle when the rod piece (451) is pushed one time such that a user can easily control the dropping amount to the container of the scale (18). Moreover, a user can remove the cap (432) from the storage container (40), and directly pull out and change a measuring rod (43) which has a desired-sized measuring tank (431) to control the amount of single dropping.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. A food storage cabinet comprising:
a main body having an interior space, a storage room, and a second room which is configured for withdrawing stored food, and a controller, which is installed in the interior space, electrically connected to a motor; the motor comprising a spindle positioned inside the storage room, and a suction nozzle and an inflated portion respectively installed on the storage room of the main body; a first dropping opening formed between the storage room and the second room, and the second room having an air-tight door;
an inert gas cylinder, which is controlled by the controller, installed in the interior space of the main body and connected to the inflated portion through a pipe;
a vacuum unit, which is controlled by the controller, installed in the interior space of the main body and connected to the suction nozzle through a first vacuum tube; and
a storage container having a funnel-shaped inner space, and a first connecting member and a second connecting member, which are installed on the storage container, communicated with the inner space; a bottom end of the inner space having a second dropping opening; a measuring rod, which penetrates through the storage container, located adjacent to the second dropping opening, and the measuring rod comprising a measuring tank located at a position corresponding to and blocking the second dropping opening; the storage container put and secured inside the storage room of the main body, and the first connecting member and the second connecting member respectively connected to the inflated portion and the suction nozzle; the measuring rod axially connected to the spindle of the motor to have spin movement synchronously; the inert gas cylinder and the vacuum unit respectively used for maintaining the inner space of the storage container in vacuum and filled with inert gas; the motor configured to axially spin the measuring rod, and the stored food in the measuring tank of the measuring rod adapted to be dropped and pass through the first dropping opening into the second room, thereby keeping stored food fresh and providing a preset amount of stored food at a time for a user.

2. The food storage cabinet of claim 1, wherein an operating unit, which is configured to operate the measuring rod to drop stored food manually, is installed adjacent to the measuring rod of the storage container.

3. The food storage cabinet of claim 2, wherein the operating unit comprises a rod piece, a first spring, a toothed bar and a toothed disc; an end of the rod piece coupled to the first spring is adapted to stick out of the storage container for a user to push while another end of the rod piece is engaged with the toothed bar; the toothed disc is installed on the storage container, and a gear rod extending from a surface of the toothed disc is configured to engage with the toothed bar to have synchronous movements; and a gear is installed on the spindle of the motor to engage with the toothed disc such that by pushing the rod piece, the toothed bar is configured to drive the gear and the measuring rod through the gear rod and the toothed disc to have spin movements synchronously, thereby achieving manual dropping process.

4. The food storage cabinet of claim 3, wherein the storage container has a locating groove, and a column extended from a surface of the toothed bar is adapted to be inserted and move along the locating groove, thereby achieving the engaging and disengaging processes between the toothed bar and the gear rod.

5. The food storage cabinet of claim 1, wherein a lateral surface of the storage container has a cap located at a position corresponding to an end of the measuring rod, so that after the cap is removed, the measuring rod is configured to directly be pulled out and replaced by a measuring rod having a desired-sized measuring tank to control the amount of single dropping.

6. The food storage cabinet of claim 1, wherein a top end of the inner space of the storage container is connected to an openable lid, and the storage container has a handle which is communicated with the inner space, and the handle comprises a release button which is adapted to release vacuum status of the inner space to enable the lid to be opened.

7. The food storage cabinet of claim 1, wherein a second vacuum tube is connected between the vacuum unit and a vacuum nozzle, and the vacuum nozzle is communicated with the second room to create a vacuum in the second room.

8. The food storage cabinet of claim 1, wherein, the second room comprises a germicidal lamp and a scale, which are electrically and respectively connected to the controller.

9. The food storage cabinet of claim 1, wherein the first connecting member has a second spring and a first ball body installed therein, and the second spring is configured to bear against the first ball body and an end of the first connecting member at two ends thereof to push the first ball body outwardly, and the second connecting member comprises a third spring and a second ball body installed therein, and the third spring is configured to bear against the second ball body and an end of the second connecting member at two ends thereof to push the second ball body outwardly, thereby maintaining the storage container in sealing state; the storage container is configured to be maintained in vacuum or be filled with inert gas both when been secured in and taken out from the main body, and the suction nozzle has a protruding push rod which is configured to push away the first ball body of the first connecting member.

10. The food storage cabinet of claim 1, wherein the storage container comprises a metal piece, and the storage room has a magnetic member which is configured to attract and hold the metal piece, thereby securing a position of the storage container.

* * * * *